United States Patent
Seaver et al.

(10) Patent No.: US 10,251,673 B2
(45) Date of Patent: Apr. 9, 2019

(54) MULTIPLE SECTION TROCAR

(71) Applicant: ARKIS BIOSCIENCES INC., Knoxville, TN (US)

(72) Inventors: Chad Seaver, Knoxville, TN (US); James Alexander Killeffer, Knoxville, TN (US); Chris Arnott, Knoxville, TN (US)

(73) Assignee: Arkis Biosciences Inc., Knoxville, TN (US)

( * ) Notice: Subject to any disclaimer, the term of this patent is extended or adjusted under 35 U.S.C. 154(b) by 1075 days.

(21) Appl. No.: 13/858,632

(22) Filed: Apr. 8, 2013

(65) Prior Publication Data

US 2013/0267982 A1 Oct. 10, 2013

Related U.S. Application Data

(60) Provisional application No. 61/621,509, filed on Apr. 7, 2012.

(51) Int. Cl.
*A61B 17/34* (2006.01)
*A61M 27/00* (2006.01)
*A61B 17/32* (2006.01)

(52) U.S. Cl.
CPC ...... *A61B 17/3468* (2013.01); *A61B 17/3403* (2013.01); *A61B 2017/320056* (2013.01); *A61M 27/006* (2013.01)

(58) Field of Classification Search
CPC ........ A61B 2017/0472; A61B 17/0485; A61B 17/3403; A61M 27/002; A61M 27/00; A61M 27/006
USPC .......... 606/139, 144, 145, 147, 148
See application file for complete search history.

(56) References Cited

U.S. PATENT DOCUMENTS

| | | | |
|---|---|---|---|
| 2004/0230207 A1* | 11/2004 | Gellman | A61B 17/00234 606/148 |
| 2005/0085715 A1* | 4/2005 | Dukesherer | A61B 5/06 600/424 |
| 2005/0090852 A1* | 4/2005 | Layne | A61B 17/3417 606/190 |

\* cited by examiner

*Primary Examiner* — Eric Rosen
*Assistant Examiner* — Chima Igboko
(74) *Attorney, Agent, or Firm* — Meunier Carlin & Curfman LLC

(57) ABSTRACT

A medical device insertion system, and a method of using the system, to mate trocars inside a patient during a medical procedure, the system including a first trocar having a first end to insert into a patient, and a second end at which a first user control is provided, and a second trocar having a first end to insert into a patient, and a second end at which a second user control is provided, wherein the respective first ends of the first and second trocars are formed so as to mate to one another inside the patient to form a continuous path between the respective second ends.

11 Claims, 3 Drawing Sheets

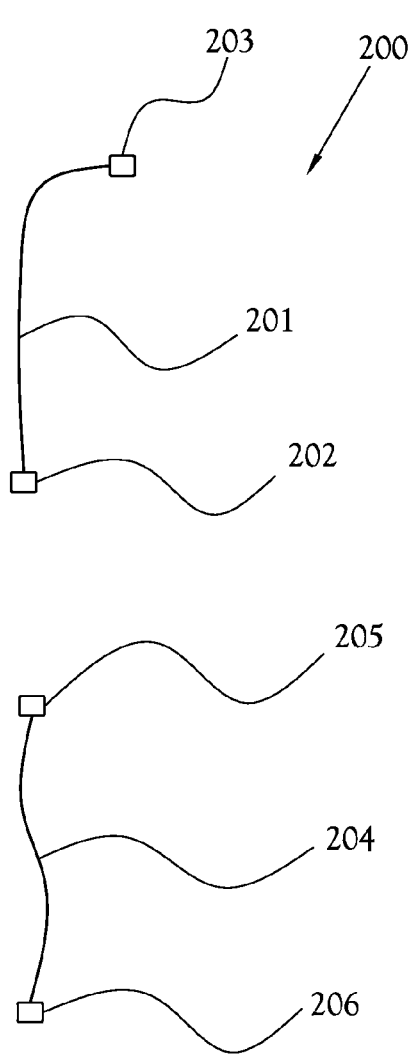
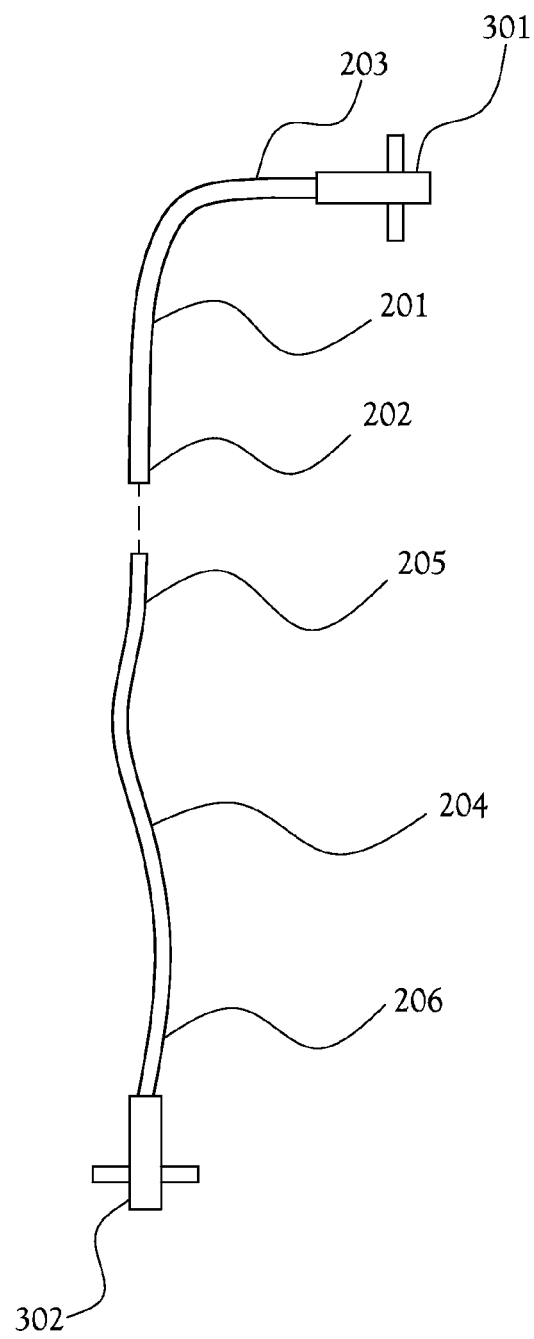
Fig.2
Fig.3

MULTIPLE SECTION TROCAR

CROSS-REFERENCE TO RELATED APPLICATIONS

This application claims priority from U.S. Provisional Application No. 61/621,509, filed on Apr. 7, 2012.

FIELD OF INVENTION

The present general inventive concept relates generally to a system and method to mate instruments in a patient, and, more particularly, to a multiple section medical instrument to be mated inside a patient to form a continuous path between entry points of the multiple sections.

BACKGROUND

Conventionally, in the case of a hydrocephalus shunt surgical installation procedure with the catheter located at the top of the patient's skull, three incisions are required to install the hydrocephalus shunt. FIG. 1 is a schematic illustration the conventional incision locations performed in a conventional hydrocephalus shunting system installation procedure. Referring to FIG. 1, the incision locations applied to a patient during a hydrocephalus shunt surgical installation procedure are generally indicated by 100. The box shapes at the incision locations are intended to indicate the general area of the incisions, rather than the shape or size of the incisions. These three incisions are located at the patient's scalp forming a first incision 101, abdomen forming a second incision 102, and the base of the patient's neck forming a third incision 103. Once the incisions are made the shunt tubing is subcutaneously tunneled from the abdomen incision 102 to the third incision 103, using, for example, a long trocar, which may also be referred to as a tunneler, and/or inserter, and/or introducer. Then the shunt tubing is further manually subcutaneously tunneled by common surgical hand tools, such as forceps, from the third incision 103 to the first incision 101, forming a complete and continuous subcutaneous path between the first and second incisions. The third incision 103 is generally required because the extreme curvilinearity of the path between the first and second incisions 101 and 102, and prevents direct tunneling between the first and second incisions with a typical semi-ridged, manipulable trocar tunneling instrument. It is advantageous to minimize the number of incisions required to perform a surgical procedure in order to minimize bodily trauma, possibility of infection, and recovery time.

Therefore, there exists a desire for a surgical tool that allows the surgeon to route the drainage tube between the first and second incisions without the third incision to both increase surgical productivity and minimize patient trauma.

BRIEF SUMMARY

The present general inventive concept provides a medical device insertion system, and a method of using the system, to mate instruments inside a patient during a medical procedure to avoid excessive incisions made to the patient. Instruments such as trocars may be mated inside the patient to form a continuous path from a first incision to a second incision. Various example embodiments provide a multi-section instrument to subcutaneously tunnel a path between incisions with a minimum number of incisions, and implant a device routed through the interior connection during a hydrocephalous installation surgery, using an instrument such as a multi section trocar.

Additional aspects and advantages of the present general inventive concept will be set forth in part in the description which follows, and, in part, will be obvious from the description, or may be learned by practice of the present general inventive concept.

The foregoing and/or other aspects and advantages of the present general inventive concept may be achieved by a method of blindly mating instruments during a surgical procedure, the method including inserting a first instrument into a first entry point, the first instrument having a first and second endpoint and a first removable stylet, inserting a second instrument into a second entry point, the second instrument having a first and second endpoint and a second removable stylet, tunneling the first and second instruments to an intersection point some distance from the first and second instrument entry points, such that the second endpoint of the first instrument intersects the position of the second endpoint of the second instrument, and the second endpoint of the second instrument intersects the position of the second endpoint of the first instrument, removing the first and/or second stylets from the first and second instruments, and blindly mating the first and second instruments at their second endpoints to form a connection between the first and second instrument, wherein the blindly connected instruments form a continuous path between the first and second instruments entry points.

The second instrument may be a larger size, relative to the first instrument, allowing the insertion of the first instrument's second endpoint into the second endpoint of the second instrument to form the continuous path through both instruments.

The second end points of the first and second instrument may be constructed with an attractive material and/or shape that assists in the blind mating between the first and second instruments.

The first instrument may be configured to pass completely through the second instrument.

A liquid, gas, wire, tube, and/or other instrument may be passed through the instruments and/or continuous path formed by the blindly mated instruments.

The instruments may include controllable guidance assistance to blindly mate the instruments.

The mated instruments may form a temporary path for the installation of at least one medical device, and the instruments may be removed to permanently install the medical device.

The second endpoint of the second instrument may be formed to allow the blind mating of multiple first instruments second endpoints.

The multiple blindly mated instruments may form a network of subcutaneous connections for the installation of at least one medical device or a network of medical devices.

The second endpoints of the first and second instruments may be adjustable, and the adjustment may aid the blind mating of the first and second instruments.

The foregoing and/or other aspects and advantages of the present general inventive concept may also be achieved by a method of blindly mating trocars during a surgical procedure, the method including inserting a first trocar section into a first entry point, the first trocar having a first and second endpoint and a first removable stylet, inserting a second trocar section into a second entry point, the second trocar having a first and second endpoint and a second removable stylet, tunneling the first and second trocars to an intersection point some distance from the first and second trocar entry points such that the second endpoint of the first trocar intersects the position of the second endpoint of the second trocar, and the second endpoint of the second trocar intersects the position of the second endpoint of the first trocar, removing the first and second stylets from the first and second trocars, and blindly mating the first and second trocars at their second endpoints to form a connection through the first and second trocars, wherein the blindly connected trocars form a continuous path between the first and second trocar entry points.

The second trocar may be a larger size, relative to the first trocar, allowing the insertion of the first trocar's second endpoint into the second endpoint of the second trocar to form a continuous path through both trocars.

The second end points of the first and second trocar may be constructed with an attractive material and/or shape that assists in the blind mating between the first and second trocars.

The first trocar may be configured to pass completely through second trocar.

A liquid, gas, wire, tube, and/or other instrument may be passed through the connection formed by the blindly mated trocars.

The trocars may include controllable guidance assistance to blindly mate the trocars.

The mated trocars may form a temporary path for the installation of at least one medical device, and the trocars may be removed to permanently install the medical device.

The second endpoint of the second trocar may be formed to allow the blind mating of multiple first trocar second endpoints.

The multiple blindly mated trocars may form a network of subcutaneous connections for the installation of at least one medical device or a network of medical devices.

The second endpoints of the first and second trocar may be adjustable, and the adjustment may aid the blind mating of the first and second trocars.

The foregoing and/or other aspects and advantages of the present general inventive concept may also be achieved by a method of mating instruments during a surgical procedure, the method including inserting a first endpoint of a first instrument into a first entry point of a patient, the first instrument having a first removable stylet, inserting a first endpoint of a second instrument into a second entry point of the patient, the second instrument having a second removable stylet, tunneling the first and second instruments such that the respective first endpoints meet at a common point some distance from the first and second instrument entry points, mating the respective first endpoints of the first and second instruments, and removing the first and second stylets from the first and second instruments, wherein the mated instruments form a continuous path between respective second endpoints of the first and second instruments.

The first instrument may have a diameter sufficiently larger than at least a portion of the second instrument such that at least the smaller portion of the second instrument fits inside the first instrument in the mating of the first and second instruments.

The smaller portion of the second instrument may be tapered to be of a smaller diameter than a remaining portion of the second instrument.

The second instrument may be configured so as to pass through substantially all of the first instrument.

The respective first endpoints may be formed of a material to attract one another.

A liquid, gas, wire, tube, other instrument, or any combination thereof may be passed through the continuous path between the respective second endpoints.

The method may further include using controllable guidance assistance provided to at least one of the first and second instruments during the mating of the first and second instruments.

The method may further include installing at least one medical device through the continuous path.

The method may further include removing the first and second instruments in response to the installing of the at least one medical device.

The method may further include determining position inside the patient off the first and/or second endpoints according to sensors provided to the respective first and/or second endpoints of the instruments.

The mating may include manipulating user controls at a second endpoint of the first and/or second instruments to control movement of the corresponding first endpoints.

The controlled movement may include curving, opening, closing, locking, or any combination thereof of the corresponding first endpoints.

The first and/or second instruments may be trocars.

The foregoing and/or other aspects and advantages of the present general inventive concept may also be achieved by a medical device insertion system to mate trocars inside a patient during a medical procedure, the system including a first trocar having a first end to insert into a patient, and a second end at which a first user control is provided, and a second trocar having a first end to insert into a patient, and a second end at which a second user control is provided, wherein the respective first ends of the first and second trocars are formed so as to mate to one another inside the patient to form a continuous path between the respective second ends.

The system may further include first and second stylets respectively coupled to the corresponding first and second user controls, the first and second stylets formed so as to be removable after the first and second trocars are mated to one another to form a hollow path between the respective second ends.

The first trocar may have a diameter sufficiently larger than at least a portion of the second trocar such that at least the smaller portion of the second trocar fits inside the first trocar in response to the mating of the first and second trocars.

The smaller portion of the second trocar may be tapered to be of a smaller diameter than a remaining portion of the second trocar.

The second trocar may be configured to pass through substantially all of the first trocar.

The respective first ends may be formed of a material such that the respective first ends attract one another.

The system may further include sensors provided to at least one of the respective first ends to determine a position thereof inside the patient.

The first and/or second user controls may include manipulation controls to perform operations including curving, opening, closing, locking, or any combination thereof of the corresponding first ends.

The system may further include one or more additional trocars with corresponding first ends formed so as to mate with the respective first ends of the first and second trocars to form a plurality of continuous and connected paths in the patient.

Other features and aspects may be apparent from the following detailed description, the drawings, and the claims.

BRIEF DESCRIPTION OF THE FIGURES

The following example embodiments are representative of example techniques and structures designed to carry out the objects of the present general inventive concept, but the present general inventive concept is not limited to these example embodiments. In the accompanying drawings and illustrations, the sizes and relative sizes, shapes, and qualities of lines, entities, and regions may be exaggerated for clarity. A wide variety of additional embodiments will be more readily understood and appreciated through the following detailed description of the example embodiments, with reference to the accompanying drawings in which:

FIG. 2 is a schematic illustration of a multiple section trocar subcutaneous tunneling instrument according to an example embodiment of the present general inventive concept;

FIG. 3 is a more detailed illustration of the multiple section trocar subcutaneous tunneling instrument according to an example embodiment of the present general inventive concept.

DETAILED DESCRIPTION

Figure 1:
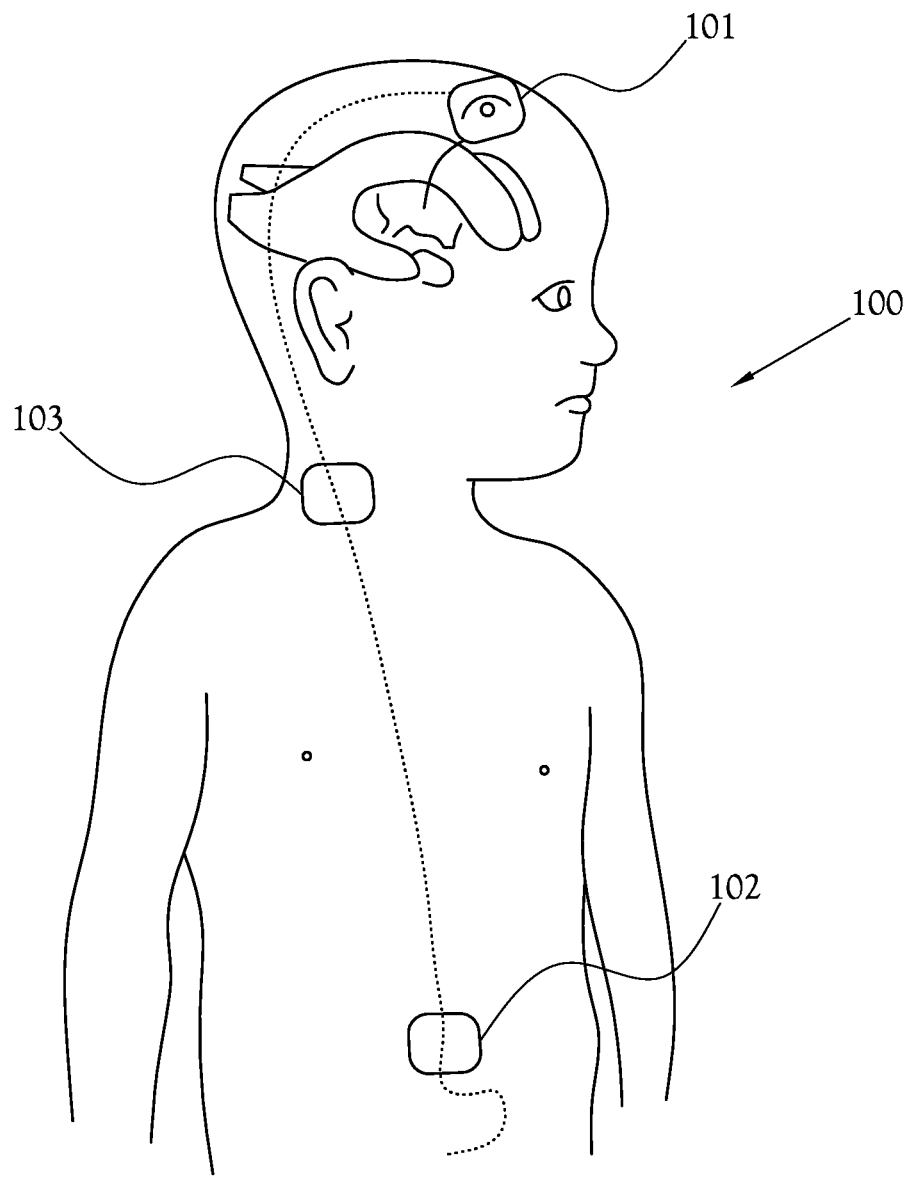
FIG. 1 is a schematic illustration the conventional incision locations performed in a conventional hydrocephalus shunting system installation procedure.

Reference will now be made to various example embodiments of the present general inventive concept, examples of which are illustrated in the accompanying drawings and illustrations. The example embodiments are described herein in order to explain the present general inventive concept by referring to the figures.

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. The described progression of processing operations described are merely examples, however, and the sequence of operations is not limited to that set forth herein and may be changed as is known in the art, with the exception of operations necessarily occurring in a certain order. Also, description of well-known functions and constructions may be omitted for increased clarity and conciseness.

Note that spatially relative terms, such as "up," "down," "right," "left," "beneath," "below," "lower," "above," "upper" and the like, may be used herein for ease of description to describe one element or feature's relationship to another element(s) or feature(s) as illustrated in the figures. Spatially relative terms are intended to encompass different orientations of the device in use or operation in addition to the orientation depicted in the figures. For example, if the device in the figures is turned over or rotated, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Various example embodiments of the present general inventive concept, as described herein, provide a medical device insertion system, and a method of using the system, to mate instruments inside a patient during a medical procedure to avoid excessive incisions made to the patient. Instruments such as trocars may be mated inside the patient to form a continuous path from a first incision to a second incision. Various example embodiments provide a multi-section instrument to subcutaneously tunnel a path between incisions with a minimum number of incisions, and implant a device routed through the interior connection during a hydrocephalous installation surgery, using an instrument such as a multi section trocar.

In various example embodiments described herein, multi section tunneling trocars represent the multi section instruments of the present general inventive concept. However, it is understood that the instruments which may be utilized in the systems and methods of the present general inventive concept are not limited to trocars, tunneling or otherwise. Also, in various example embodiments the terms "blind" or "blindly" are used to indicate a mating of the instruments that are performed inside a patient's body that may not be viewable by the naked eye.

Various example embodiments of the present general inventive concept provide a multiple section blind-mating or self-aligning subcutaneous tunneling trocar. Example embodiments of the present general inventive concept may be used, for example, to form blind-mating or self-aligning subcutaneous tunnels during surgical procedures.

Such advantages as described herein, as well as other advantages not explicitly described herein, overcome many of the previously described limitations of the conventional hydrocephalus shunt installation surgical procedure by providing a novel blind-mating or self-aligning multiple section instrument such, as a trocar, which then allows for the continuous subcutaneous tunneling of hydrocephalus drainage tube and the elimination of third incision.

FIG. 2 is a schematic illustration of a multiple section trocar subcutaneous tunneling instrument according to an example embodiment of the present general inventive concept. A multiple section blind-mating or self-aligning subcutaneous trocar according to this example embodiment is indicated generally by 200. It is noted that although a trocar is described in the example embodiment of FIG. 2, various other mate-able multi section instruments may be used according to other various example embodiments of the present general inventive concept.

The multiple section blind-mating or self-aligning subcutaneous tunneling trocar illustrated in FIG. 2 includes a first semi-rigid trocar 201 having a first end 202 and a second end 203, which may be subcutaneously tunneled from the first incision 101 to an approximate location where the conventional incision 103 may have been located. It is noted that the squares illustrated for elements 202,203,205,206 merely serve to indicate the locations of the ends of the multiple sections of the illustrated instrument, and do not imply any of the various example devices or configurations that may be provided at some of those points. A second semi-ridged trocar 204 with a first end 205 and a second end 206 may be subcutaneously tunneled from the second incision 102 to an approximate location where the conventional incision 103 may have been located.

Generally, trocar surgical instruments are round with a fixed diameter extending across the length of the trocar and contain a core that can be removed after subcutaneous tunneling, leaving behind the empty outer tube for the later placement of the hydrocephalus drainage tube or other connecting/communicating device. In various example embodiments, the removable core may be any of a number of different types and/or configurations of stylets. In some example embodiments, the stylets may be chosen based on the type of procedure, bodily material through which the trocar instrument(s) will be moving, and/or other preferences of the user. In various example embodiments, these different stylets may all be usable with the same trocar instrument.

In various example embodiments of the present general inventive concept, the first trocar 201 may have a larger diameter, or other blind-mate interface, than that of the second trocar 204, such that the second trocar 204 can be blindly mated or self-aligned and received into the larger diameter of the first trocar 201. However, other various example embodiments may include mating configurations of multiple sections of instruments having the same diameter. This blind-mate or self-alignment of the first and second trocars 201,204 may be accomplished by other means familiar to one skilled in the art such as, but not limited to, a tapered diameter trocar, a circular or rectangular funnel shaped endpoint on the receiving trocar, electronic/mechanical geospatial direction finding/control, etc.

After mating the first and second trocars 201,204, a tube, wiring, and/or other device(s) may be routed through the completed path between the first and second incisions 101 and 102. This allows for a continuous subcutaneous path through first and second trocars 201,204 for the placement of the aforementioned tubing, wiring, and/or any other physical connection media between the first and second incisions 101,102 after the trocars are removed. It can also be appreciated by one of ordinary skill in the art that, in various example embodiments of the present general inventive concept, the second trocar 204 may be configured so as to be inserted entirely through the first trocar 201 so that the second trocar 204 forms a complete path between the first and second incisions 101 and 102. Other mechanical, electromechanical, or electronic guidance means can be placed on or around the trocar to aid positioning before or during blind-mating or self-alignment.

FIG. 3 is a more detailed illustration of a multiple section trocar subcutaneous tunneling instrument according to an example embodiment of the present general inventive concept. Similar elements of the example embodiment illustrated in FIG. 3 share common identifiers with the corresponding elements of FIG. 2. As illustrated in FIG. 3, the trocars 201,204 are provided on one end 203,206 thereof with manipulation controls 301,302 that aid in the blind guidance and mating of the other ends 202,205 of the trocars.

It is noted that the use of a blind-mating trocar to create subcutaneous paths is not limited to the surgical installation of a hydrocephalous shunt system, but may be used in various other surgeries in which subcutaneous tunneling is required. Furthermore, as illustrated in FIG. 3, a handle or manipulation device 301,302 may be attached to endpoints 203,206 of trocars 201,204 to help provide additional force while positioning trocars 201,204. Such manipulation devices may, for example, modify opposite endpoints for mechanical manipulation, including curvature, opening and closing, an electronic guidance control, locking to the mating trocar, etc. In various example embodiments, the trocars may be formed with such a manual adjustment, or manipulation device, so that a user may use the manual adjustment to adjust, curve, twist, etc., or otherwise form the shape of the trocar, or portions of the trocar, to assist in the subcutaneous tunneling. Also, in various example embodiments, the trocars may be formed to have a blunt tip, or a sharp tip, and/or various angles and/or length of a tapered configuration. Thus, in some example embodiments, the trocar may have a blunt endpoint at which the stylet provides a sharper point used the tunneling, and in some example embodiments, the trocar may have a sharper point to perform the tunneling. In still other embodiments, both the trocar and the stylet may have complementing or otherwise various degrees of sharpness to work in conjunction during the tunneling procedure.

Figure 4B:
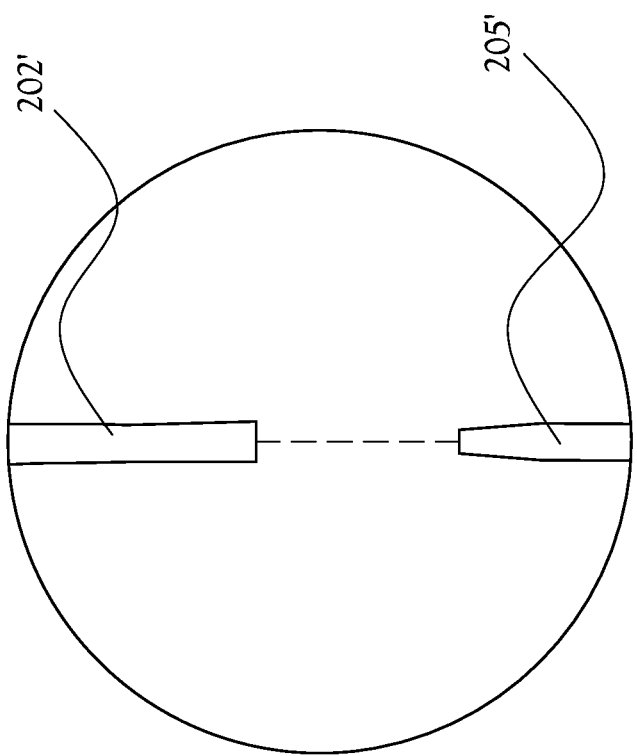
FIGS. 4A-4B illustrate example embodiments of mating ends of the multiple section trocar subcutaneous tunneling instrument according to example embodiments of the present general inventive concept.
Figure 4A:
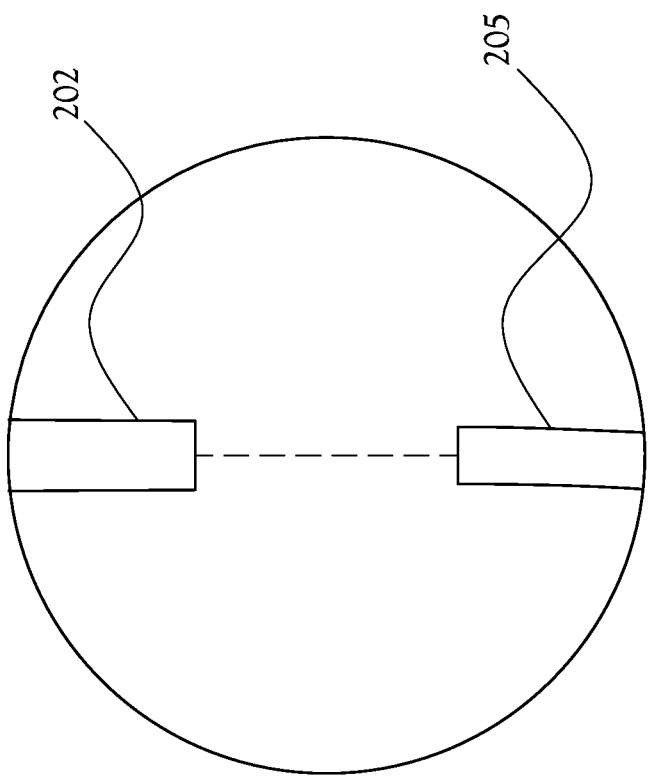

FIGS. 4A-4B illustrate example embodiments of mating ends of the multiple section trocar subcutaneous tunneling instrument according to example embodiments of the present general inventive concept. FIG. 4A illustrates an example embodiment in which two sections of an instrument such as a trocar have different diameters, the end 205 is able to fit inside the end 202 during the mating of the two sections. FIG. 4B illustrates an example embodiment in which two sections of an instrument such as a trocar have substantially similar diameters, and wherein at least a portion of the end 205' of one of the trocars is tapered so as to fit inside the end 202' of the other trocar to perform, or at least initiate, the mating of the two sections.

While the example embodiments illustrated in FIGS. 4A-4B show the trocar sections being configured to mate at the direct endpoints thereof, in various other example embodiments at least one of the trocar sections may be configured with a side entry point for the mating procedure. For example, some embodiments may have a solid end point of at least one of the trocars, the end point being sharp or blunt or various levels of a tapered end, and a mating end of the core instrument may be accessible at a point on the side of the trocar proximate to the tunneling end. The internal channel of the trocar with the side entry point, and thus the core instrument such as the stylet, may be curved to assist the receiving and/or directing of the other trocar. In such an example, a first trocar having the side entry point may be used to tunnel to a point farther than the mating point of the two trocars, and the second trocar may meet the first trocar at that side entry point to perform the mating procedure, the end point of the second trocar being aligned with the side entry point of the first trocar.

Additionally, several blind-mating trocar could be routed to connect to a common location(s) to form a multiple path subcutaneous branch/node(s) within the body for subcutaneous connections of multiple biological areas for diagnosis and/or treatment(s). These subcutaneous branch/nodes(s) could link several different communication/transfer types such as electrical, mechanical, electromechanical, tubing, etc., to/from different areas within the body to form a network of diagnostic and/or treatment device(s).

According to various embodiments of the present general inventive concept, a medical device insertion system, and a method of using the system, is provided to mate instruments, or sections of an instrument, inside a patient during a medical procedure to avoid excessive incisions made to the patient. Instruments such as trocars may be mated inside the patient to form a continuous path from a first incision to a second incision. Various example embodiments provide a multi-section instrument to subcutaneously tunnel a path between incisions with a minimum number of incisions, and implant a device routed through the interior connection during a hydrocephalous installation surgery, using an instrument such as a multi section trocar.

It is noted that the simplified diagrams and drawings do not illustrate all the various connections and assemblies of the various components, however, those skilled in the art will understand how to implement such connections and assemblies, based on the illustrated components, figures, and descriptions provided herein, using sound engineering judgment.

Numerous variations, modifications, and additional embodiments are possible, and accordingly, all such variations, modifications, and embodiments are to be regarded as being within the spirit and scope of the present general inventive concept. For example, regardless of the content of any portion of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated.

While the present general inventive concept has been illustrated by description of several example embodiments, it is not the intention of the applicant to restrict or in any way limit the scope of the inventive concept to such descriptions and illustrations. Instead, the descriptions, drawings, and claims herein are to be regarded as illustrative in nature, and not as restrictive, and additional embodiments will readily appear to those skilled in the art upon reading the above description and drawings.

The invention claimed is:

1. A method of mating instruments during a surgical procedure, the method comprising:
    inserting an end of a first instrument into a first entry point through a scalp of a patient;
    inserting an end of a second instrument into a second entry point through an abdomen of the patient, the ends of the first and second instruments being configured to align with one another upon mating of the ends;
    tunneling the end of the first instrument subcutaneously around the patient's skull from the first entry point until the end of the first instrument is proximate a neck of the patient;
    tunneling the end of the second instrument subcutaneously from the second entry point until the end of the second instrument is proximate the neck of the patient; and
    tunneling the first and second instruments such that the ends of the first and second instruments are mated with one another proximate the neck of the patient and aligned to form a continuous subcutaneous path between the first and second entry points.

2. The method of claim 1, wherein the second instrument is a larger size, relative to the first instrument, facilitating the alignment of the ends upon mating.

3. The method of claim 2, wherein the first instrument is configured to pass completely through the second instrument.

4. The method of claim 1, further comprising passing a tube through the continuous path.

5. The method of claim 1, wherein the first and second instruments include user controls to facilitate tunneling of the first and second instruments and mating of the ends of the first and second instruments.

6. The method of claim 5, wherein the user controls are configured to perform operations including curving, opening, closing, locking, or any combination thereof of the corresponding ends of the first and/or second instruments.

7. The method of claim 1, wherein the ends of the first and second instruments are adjustable to facilitate the aligning and/or mating of the ends of the first and second instruments.

8. The method of claim 1, wherein the first and second instruments are trocars.

9. The method of claim 1, wherein the first instrument has a diameter sufficiently larger than at least a portion of the second instrument such that at least the smaller portion of the second instrument fits inside the first instrument in the mating of the first and second instruments.

10. The method of claim 9, wherein the smaller portion of the second instrument is tapered to be of a smaller diameter than a remaining portion of the second instrument.

11. The method of claim 1, wherein tunneling of the first instrument includes tunneling the first instrument subcutaneously along a curve of the skull of the patient.

* * * * *